United States Patent [19]
King et al.

[11] Patent Number: 5,838,840
[45] Date of Patent: Nov. 17, 1998

[54] INSPECTION DEVICE USING A FIELD MODE VIDEO CAMERA WITH INTERPOLATION TO REPLACE MISSING PIXELS

[75] Inventors: Edwin E. King, Lombard; Daniel T. Trabbic, Elmhurst; Richard M. O'Grady, Chicago; Brian S. Patrick, Westmont, all of Ill.

[73] Assignee: BST/Pro Mark, Elmhurst, Ill.

[21] Appl. No.: 705,200

[22] Filed: Aug. 29, 1996

[51] Int. Cl.$^6$ .................................................... G06K 9/32
[52] U.S. Cl. ........................... 382/300; 348/96; 348/132; 348/135; 348/175; 348/264; 348/282; 348/430; 348/439; 348/463; 356/430; 382/299; 396/272
[58] Field of Search ................................... 382/300, 299; 348/96, 264, 439, 135, 132, 458, 282, 175, 463; 356/430; 364/525; 396/272

[56] References Cited

U.S. PATENT DOCUMENTS

| | | |
|---|---|---|
| 4,922,909 | 5/1990 | Little et al. .............................. 128/630 |
| 4,951,139 | 8/1990 | Hamilton et al. ......................... 358/135 |
| 5,040,057 | 8/1991 | Gilblom et al. .......................... 358/101 |
| 5,414,270 | 5/1995 | Handerson et al. ..................... 250/572 |
| 5,440,648 | 8/1995 | Roberts et al. .............................. 382/8 |
| 5,469,209 | 11/1995 | Gunday et al. ............................ 348/96 |
| 5,475,617 | 12/1995 | Castonguay .............................. 364/525 |
| 5,572,433 | 11/1996 | Falconer et al. .................... 364/471.01 |
| 5,602,588 | 2/1997 | Kusaka ..................................... 348/264 |
| 5,606,410 | 2/1997 | Peelier et al. ............................ 356/237 |
| 5,646,682 | 7/1997 | Sogabe et al. ........................... 348/135 |

*Primary Examiner*—Andrew W. Johns
*Assistant Examiner*—Kanji Patel
*Attorney, Agent, or Firm*—Oblon, Spivak, McClelland, Maier & Neustadt, P.C.

[57] ABSTRACT

A video inspection device using a field mode CCD camera. In order to inspect the printing on a moving web, a field mode CCD camera is provided with a zoom lens and strobe light. The image obtained is processed so that only alternate pixels of the image are stored. When reading out the stored image, the image is blown up by a factor of two and the missing pixels are interpolated horizontally and vertically. The resultant image is displayed in a monitor for the operator to inspect.

9 Claims, 3 Drawing Sheets

INSPECTION DEVICE USING A FIELD MODE VIDEO CAMERA WITH INTERPOLATION TO REPLACE MISSING PIXELS

BACKGROUND OF THE INVENTION

1. Field of the Invention

The present invention relates generally to video inspection devices to determine print quality and more specifically to a color video inspection device for determining print quality on web presses utilizing a field mode CCD camera.

2. Discussion of the Background

Well-known web printers are used to apply printing to a substrate which is provided on a roll. The substrate is removed from one roll, the printing applied and the printed substrate is then placed on another roll. The printed rolls are then sent directly to the customer. The printing process is relative fast, so it is not possible to visually inspect the print while the press is operating. In the past, the print was checked at the end of the roll for quality control. However this does not indicate whether the print quality is correct in the middle of the roll. To compensate for any misprints in the middle of the roll, most printers print an additional 20 to 50% of the product above what the customer orders.

It would be preferable to perform on line inspection to ascertain the quality of the product during the printing so that it would not be necessary to print additional items. Moreover, since most presses now run at speeds about 350 feet per minute, the operator cannot determine print quality with the naked eye.

One mechanism for performing real time inspection is to use a hand held strobe light which can freeze the motion of the web. This allows for some rudimentary inspection, but has some drawbacks. The color of the strobe light can influence the perceived color of the print. Also, holding the strobe close to the web can be awkward and dangerous. However, the hand held strobes are relatively inexpensive and for a slightly higher cost, can be mounted directly to the press and thus cover large areas for inspection.

Another on line inspection process includes the use of a rotating drum of mirrors to reflect an image of the web onto an eye piece. To view different parts of the web, the eye piece is moved. To change the position along the web the drum timing has to be changed. While very good color reproduction is obtained and magnification is possible through the use of the eye piece, there are also disadvantages. The size of the unit requires the reconfiguration of the press. Also, it requires considerable time and effort to view different parts of the web.

A preferred method is to use video inspection of the web. Color frame mode CCD cameras are used to view the web virtually in real time. These cameras are placed near the end of the printing process. High intensity very fast zenon strobe lamps can be used to illuminate and freeze motion. CCTV zoom lenses with close-up adapters can provide magnification ranges from 2× to 30×. The analog video from the camera can be digitized and stored in memory so that it can be scanned and reverted back to analog video for display on a cathode ray tube (CRT).

The image on the CRT can be held under operator control. The picture can be updated as desired, for example every half second. Since the camera controls and the CRT can be placed anywhere, remote viewing and control is available. Thus, the operator can view the web at a point where they perform other tasks. It is also possible to have more than one CRT to allow all the operators to monitor print quality from any point. Zoom lenses on the camera provide both a large overview and a close-up possibility. Since the print can be magnified, the operators can monitor and set the color register. If desired, a motorized system can be automatically controlled to scan the entire area repeatedly.

While this type of system is clearly preferable to the previous devices, there remains the difficulty of the cost of the system. Considering, for example, the CRT, it is necessary to use computer monitors rather than standard TV monitors because the interlaced picture introduces flickering in the image. Computer monitors have a non-interlaced picture and excellent color reproduction.

For the camera system, frame mode CCD cameras have been the only cameras utilized. These cameras work in conjunction with strobe lights in order to freeze the motion of the web. Frame mode cameras require light integration only once for both the odd and even fields. This differs from field mode cameras which require light integration once for the odd field and a second time for the even field. Since the strobe lamp illuminates the web for only 5 microseconds, the field mode camera would only read out one illuminated field while the other field would be dark. Since the dark field causes alternate horizontal lines to be black, it is unacceptable. Accordingly, frame mode cameras have been utilized so that both the fields are illuminated.

Such systems also use zoom lens on the cameras and frame grabbers. The interlaced analog video from the camera is digitized in 16 bit or 24 bit format and stored in RAM. The memory can then be read out in a non-interlaced VGA.

In addition to the disadvantage of cost of these systems, costs are rising further because frame mode CCD color cameras are specifically increasing in cost. The market has been taken over by field mode cameras which have a higher resolution. Accordingly, the lower demand of frame mode cameras is causing their cost to rise. Also, the frame mode cameras are generally large and utilize either half inch or two-thirds inch format CCDS. These large CCDs require large zoom lenses so that the camera box length is larger, which makes it more difficult to install on the presses.

SUMMARY OF THE INVENTION

Accordingly, one object of this invention is to provide a web inspection device which is less expensive to produce.

Another object of this invention is to provide an improved web inspection device which is inexpensive and of reduced size.

A further object of this invention is to provide a web inspection device which utilizes a field mode camera.

A still further object of this invention is to provide a color video web inspection device with interpolation of pixels.

A still further object of this invention is to provide a web inspection device with a field mode CCD camera where the image is expanded and data is interpolated.

Briefly these and other objects of the invention are achieved by providing a field mode CCD camera with a small diameter diopter and a frame grabber which converts only alternate pixels into digital information. After storing, the image is expanded by a factor of two and interpolation is performed both horizontally and vertically. The resulting image is comparable to that obtained from a frame mode camera.

BRIEF DESCRIPTION OF THE DRAWINGS

A more complete appreciation of the invention and many of the attendant advantages throughout will be readily obtained as the same becomes better understood by reference to the following detailed description and considered in connection with the accompanying drawings wherein.

DESCRIPTION OF THE PREFERRED EMBODIMENTS

Figure 1:
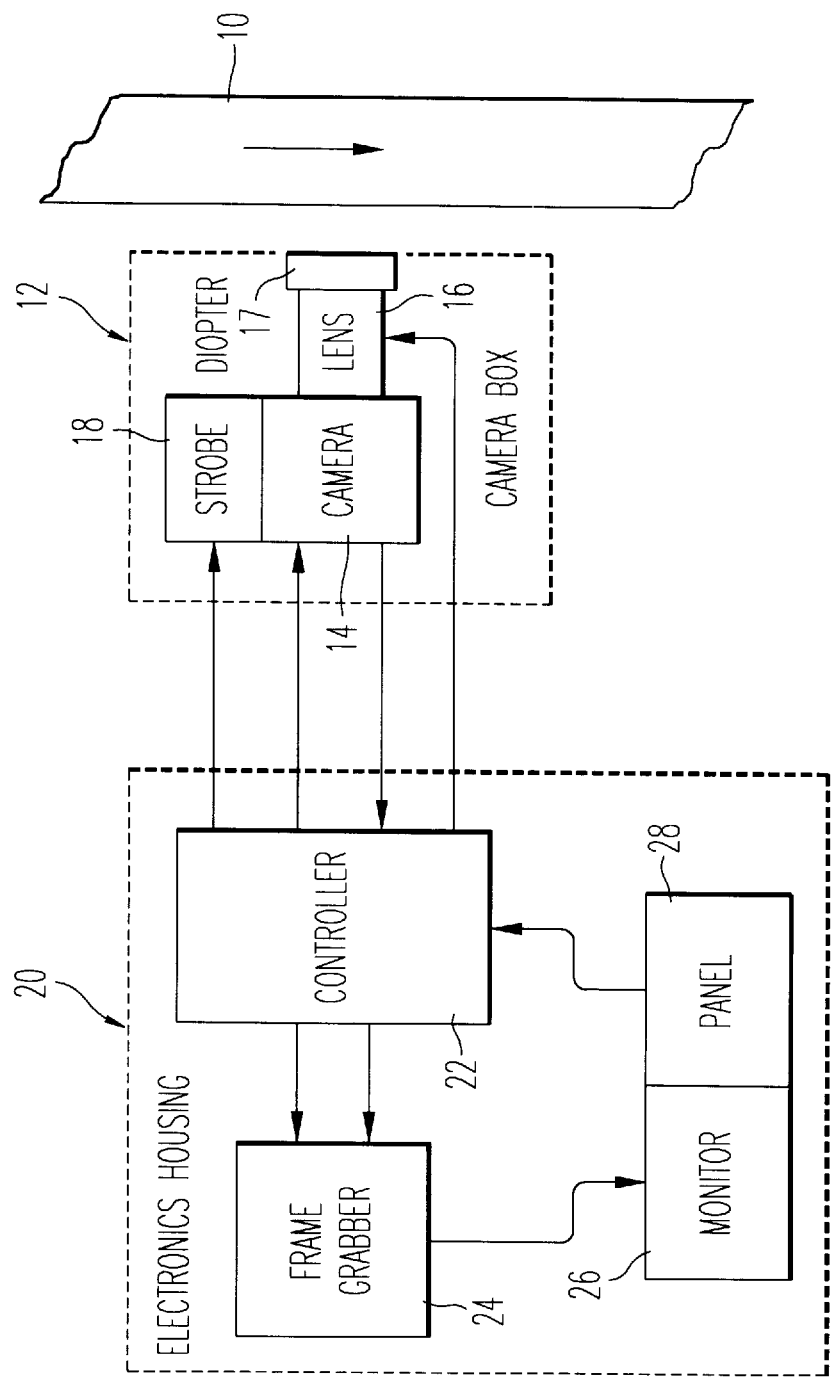
FIG. 1 is a block diagram showing the overall arrangement of the inspection device according to the present invention.

Various other objects, features and attendant advantages of the present invention will be more fully appreciated as the same becomes better understood from the following detailed description when considered in connection with the accompanying drawings in which like reference characters designate like or corresponding parts throughout the several views and wherein FIG. 1 shows the overall arrangement of the inspection device. The printed web 10 is moving from top to bottom as indicated by the arrow and is being rolled up by a roller (not seen). Prior to reaching this point, the web is unwound from another roller (not seen) and the printing apparatus forms color images on the substrate.

The camera box 12 containing the camera and related equipment is placed in the position so as to clearly view the web. The camera box may be fixedly mounted on the press equipment, or may be mounted on a motorized carrier (not shown) so that it may be scanned across the web. The camera box includes a field mode CCD camera 14 having a zoom lens 16. The zoom lens has an acromatic diopter lens 17 mounted therein to provide for closeup viewing without color distortion. The box also contains a strobe lamp 18 which shines light on the web so as to make the web appear to stop in the camera view. The zoom lens and strobe lamp are controlled from a remote position where the operator sits. However, a control panel may also be placed on the camera box 12, if desired, so that it can be controlled from nearby.

An electronics housing 20 is provided remote from the camera and near the position of the operator for controlling the camera equipment and for processing the signals therefrom. The electronics housing 20 includes a controller 22 and a frame grabber 24. The controller 22 receives the video signal from the camera 14 and processes the signal as necessary. The controller also provides controls to the zoom lens and strobe lamp as desired by the operator. The operator may input control signals through panel 28 which is then received by controller 22 and directed to the appropriate unit. The controller may adjust the zoom lens and turn on the camera and strobe lamp. The controller sends the processed video signal to the frame grabber 24. The controller also provides a control signal to the frame grabber to control its operation.

The frame grabber 24 receives the video signal, converts it into a digital signal and stores it until needed. The digital signal is then further processed before being converted back to an analog signal which is sent to monitor 26 as desired by the operator. The monitor 26 and panel 28 are in close proximity so that the operator can both view the monitor and control the input thereto.

Figure 2:
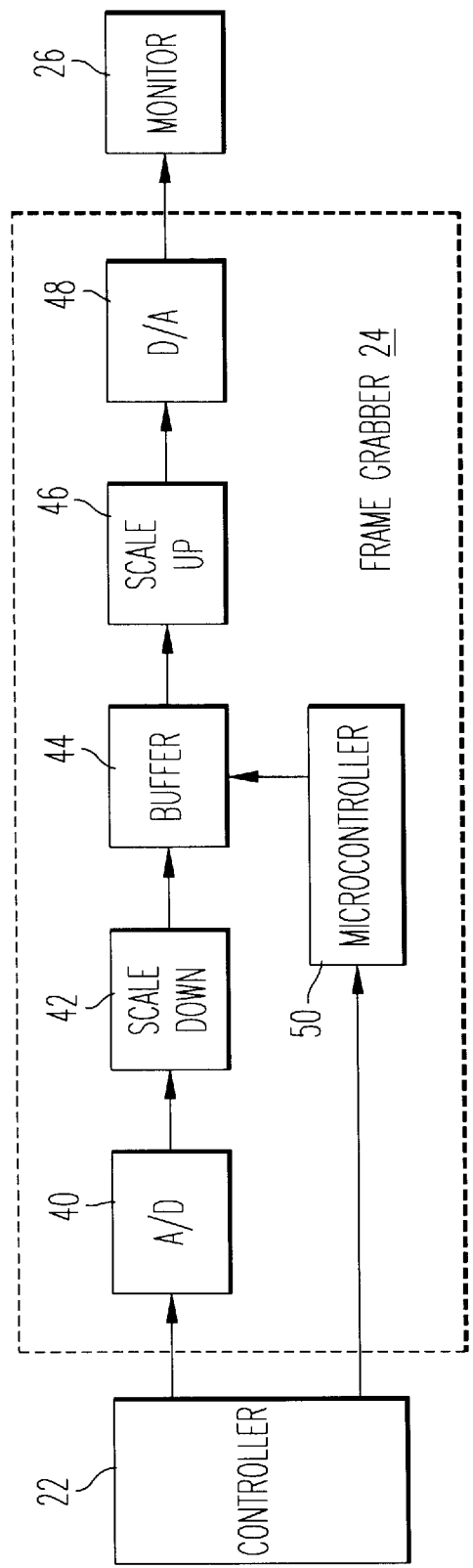
FIG. 2 is a block diagram showing the organization of the frame grabber shown in FIG. 1.

FIG. 2 shows the basic layout of the frame grabber 24. The video input from the controller 22 is received by analog to digital converter 40 which converts the signal to a digital format. The scale down unit 42 places alternate pixels of the signal in storage in buffer 44. Thus the number of pixels in the image is reduced although the aspect ratio of the original image is retained. That is, since alternate vertical lines could not be used, alternate horizontal pixels are removed so that the shape of the picture remains the same. When the image is needed, it is processed through scale up unit 46 which enlarges the image by a factor of 2 and interpolates the pixels both horizontally and vertically so as to produce a final image. By enlarging the image by a factor of 2 in both directions, the aspect ratio of the picture is retained.

The preferred form of interpolation is a linear type of pixel replicator. The input stream of bits is fed through a DDA block and then sent to a four-tap filter. This filter is the actual engine that produces the interpolation bits. In the horizontal direction, the missing bits are replaced by a simple average of the bits to either side. In the vertical direction, each bit is formed by the average of the bits above and below it. Thus this interpolation procedure actually forms average values for the missing bits rather than merely copying the previous pixel or line in order to give a more accurate image. Other types of interpolation may be used as long as they are fast enough to produce pictures at the desired rate. This signal is then converted to analog form in converter 48 and sent to monitor 26 for display. Control signals are also provided by the controller 22 to a microcontroller 50 which controls the operation of the frame grabber.

In particular, the microcontroller controls the operation of the buffer, not only in terms of the timing of storing the image and reading it out, but also in terms of imaging the display as desired within the screen. The microcontroller could also control other functions such as producing additional text to be displayed on monitor 26. The microcontroller may also store the necessary variables for powering up the unit.

Figure 3:
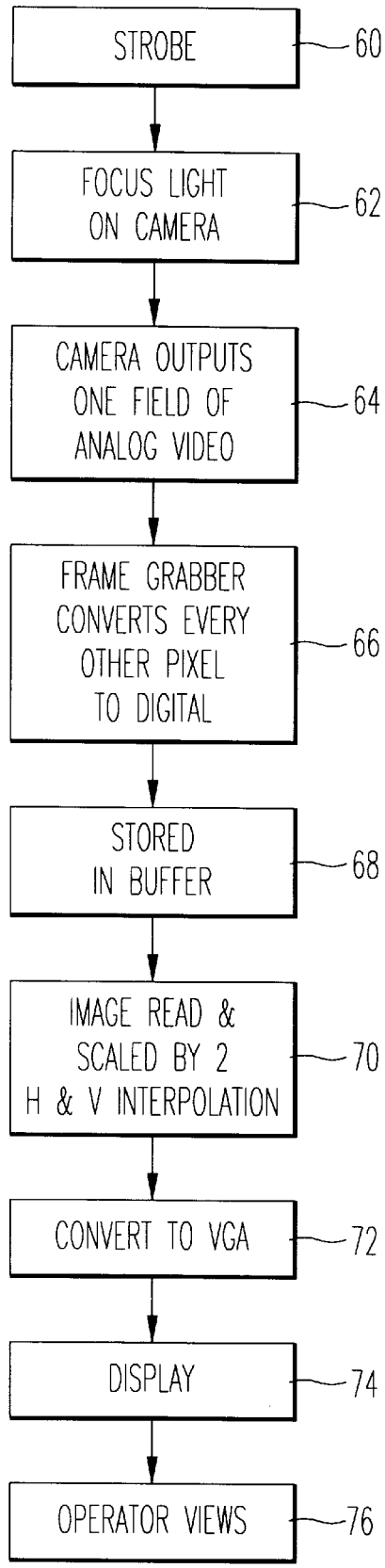
FIG. 3 is a flow chart showing the operation of the invention shown in FIG. 1.

FIG. 3 shows the basic steps of the method for inspecting the web. In step 60, the strobe lamp is illuminated for 5 microseconds under the control of controller 22. In step 62, light reflected from the web is focused on the camera 14 using the zoom lens 16 and diopter 17. In step 64, the camera outputs one field of analog video signal which is received in controller 22. In step 66, the frame grabber receives the video signal from the controller and converts every other pixel into digital information. In step 68, the digital information is then stored in buffer 44. In step 70, when the image is read, the image is enlarged by a factor of two in unit 46 and interpolation is performed both horizontally and vertically. In step 72, this signal is then converted to an analog signal in converter 48 and sent to monitor 26 for display in step 74.

In operation, it should especially be noted that the camera utilized is a field mode camera which outputs a single illuminated field rather than the traditional frame mode camera which outputs two fields. Traditionally, a field mode camera could not be utilized since the missing field caused black lines and other distortions in the display. By enlarging the stored image by a factor of two and then performing both horizontal and vertical interpolation, the image formed is considerably better than previously obtained by field mode cameras.

Furthermore, by using a field mode camera, rather than the more expensive frame mode camera, the cost of the overall system is reduced considerably. In addition, it is possible to utilize a smaller and cheaper lens assembly for this type of camera. The resultant camera box 12 is considerably smaller than that utilized in previous systems due to the smaller size of the camera and lens equipment. This makes the device easier to mount and control in operation. At the same time, the image obtained is virtually as good as in the frame camera systems.

It is also possible to use other types of image processing rather than the "enlarge by a factor of two and interpolation" described above. It could also be possible to merely display one field and eliminate the other field. However, this will distort the shape of the image since it shortens the display in the vertical direction by a factor of two. It is also possible to display one field normally and display the other field with the received black line. For some purposes, this display is sufficient although not as good as that described above.

It is also possible to utilize one field and copy the missing lines from the other field from the first field. While this covers up the black line, there is no interpolation so that diagonal lines show a staircase shape.

It would also be possible to utilize alternate pixels in one field as described in the preferred system and then copy the pixels horizontally and vertically without scaling up by a factor of two. This also produces an image which is acceptable but not as good as the preferred system, which uses true interpolation rather than merely copying.

The frame grabber has been described as receiving a YC video input and producing a VGA output to monitor 26. However, other types of signals can be utilized such as RGB signals. The device is also usable with systems utilized in other countries such as the PAL system. Also, when the video signal is digitized in converter 40, the digital bit stream form may be in the YUV422 format.

The microcontroller 50 may also control the location of the video frame in the VGA raster according to whether the data received is from an odd or even field of video. The odd field will start at the first active line of the raster while an even field will start at the second active line of the raster. This corrects for the spatial offset of the video fields. Without this correction, an even field would appear offset by one line from an odd field.

The microcontroller 50 may also be utilized to initialize the on board registers in a default state in order to obtain a display on the screen. The default register values can be stored in an I²C EEPROM (not shown) in the frame grabber. The microcontroller can generate transfer signals to controller 22 to indicate the need for the next image. This interaction between the microcontroller 50 and controller 22 enables the main controller 22 to modify the behavior of the board so that registers and memories can be written to start or stop the image grab, to enable or disable scaling, define a split screen pattern, change the display font, define the text font, etc.

The microcontroller also manages the acquisition of the image being grabbed. The image may be partially enabled so that only one part of the frame buffer is utilized. A tile effect may be accomplished by scaling down the image and changing the grab start address between two consecutive images.

The microcontroller also refreshes the memory.

Although a single buffer has been shown, it is also possible to have multiple buffers with one buffer being used to store a reference image. That image can then be copied to the live frame buffer when desired. A mask bit plane can be loaded into a buffer to define the split screen pattern desired.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for inspecting printing on a web, comprising:
   a strobe lamp for illuminating said web;
   a field mode video camera producing a video image of said web with two fields, and generating an output of a single field;
   a frame grabber receiving said output, storing alternate pixels of said output and reproducing said image by enlarging the stored pixels and interpolating both horizontally and vertically to replace a field of said video image which is not included in said output and alternate pixels which are not stored and to produce a reproduced image; and
   monitor means for displaying said reproduced image.

2. The device according to claim 1, further comprising a zoom lens on said camera.

3. The device according to claim 2, further comprising a control panel for controlling the operation of said camera, said zoom lens and said strobe lamp, said control panel being mounted near said monitor.

4. The device according to claim 2, further comprising an acromatic diopter mounted on said zoom lens.

5. The device according to claim 1, wherein said frame grabber stores said image in a buffer.

6. The device according to claim 5, wherein said frame grabber further comprises an analog to digital converter.

7. The device according to claim 5, wherein said frame grabber further comprises a digital to analog converter.

8. The device according to claim 1, wherein said frame grabber interpolates horizontally and vertically using a forward linear predictor.

9. A device for inspecting printing on a web, comprising:
   a strobe lamp for illuminating said web;
   a field mode video camera producing a video image of said web with two fields, and generating an output of a single field;
   a frame grabber receiving said output, storing pixels of said output and reproducing said image by enlarging the stored pixels and interpolating vertically to replace a field of said video image which is not included in said output and to produce a reproduced image; and
   monitor means for displaying said reproduced image.

\* \* \* \* \*